US010494683B2

(12) United States Patent
Anderson et al.

(10) Patent No.: US 10,494,683 B2
(45) Date of Patent: Dec. 3, 2019

(54) NITRATE- AND NITRITE-REDUCING PROBIOTIC FEED ADDITIVE

(71) Applicants: The United States of America, as represented by the Secretary of Agriculture, Washington, DC (US); The Texas A&M University System, College Station, TX (US)

(72) Inventors: Robin C. Anderson, College Station, TX (US); Elizabeth A. Latham, Bryan, TX (US); William E. Pinchak, Vernon, TX (US)

(73) Assignees: The Secretary of Agriculture, Washington, DC (US); The Texas A&M University System, Bryan, TX (US)

( * ) Notice: Subject to any disclaimer, the term of this patent is extended or adjusted under 35 U.S.C. 154(b) by 39 days.

(21) Appl. No.: 15/234,560

(22) Filed: Aug. 11, 2016

(65) Prior Publication Data

US 2017/0044632 A1  Feb. 16, 2017

Related U.S. Application Data

(60) Provisional application No. 62/204,112, filed on Aug. 12, 2015.

(51) Int. Cl.
| | |
|---|---|
| *A61K 35/742* | (2015.01) |
| *C12R 1/01* | (2006.01) |
| *C12N 1/20* | (2006.01) |
| *A23K 10/18* | (2016.01) |
| *A23K 50/10* | (2016.01) |
| *A23K 10/40* | (2016.01) |

(52) U.S. Cl.
CPC ............... *C12R 1/01* (2013.01); *A23K 10/18* (2016.05); *A23K 10/40* (2016.05); *A23K 50/10* (2016.05); *A61K 35/742* (2013.01); *C12N 1/20* (2013.01)

(58) Field of Classification Search
CPC ................ A61K 35/742; C12R 1/01
See application file for complete search history.

(56) References Cited

U.S. PATENT DOCUMENTS

| 6,120,810 A | 9/2000 | Rehberger et al. |
| 2006/0057118 A1 | 3/2006 | Toride et al. |

OTHER PUBLICATIONS

Borreani et al., J. Dairy Sci. 96 :5206-5216.*
Velazquez et al.,International Journal of Systematic and Evolutionary Microbiology (2004), 54, 59-64.*
Eggleton, Biochem J. Jun. 1935;29(6):1389-97.*
Sar et al., "Manipulation of rumen methanogenesis by the combination of nitrate with 1-4 galacto-oligosaccharides or nisin in sheep," Animal Feed Science and Technology, (2004), 115:129-142.
Naghmouchi et al., "Paenibacillus polymyxa JB05-01-1 and its perspectives for food conservation and medical applications," Arch Microbiol, (2011), 193:169-171.
Naghmouchi et al., "Required characteristics of Paenibacillus polymyxa JB-0501 as potential probiotic," Article in Archives of Microbiology, (Jun. 2013), 195:537-543.

\* cited by examiner

*Primary Examiner* — Taeyoon Kim
*Assistant Examiner* — Tiffany M Gough
(74) *Attorney, Agent, or Firm* — John D. Fado; Mark D. McNemar

(57) ABSTRACT

The present invention concerns novel probiotic compositions that increase nitrate- and nitrite-reduction in animals such as ruminants. The present invention thus provides compositions and methods for reducing nitrate/nitrite toxicity in such animals, or prophylactically protecting such animals from the effects of toxicity, such as methemoglobinemia. A novel strain of an unspeciated bacterial strain related to *Paenibacillus* species with nitrate- and nitrite-reducing capabilities is described. In conjunction with nitrate-supplemented diets, the probiotics of the present invention can also be utilized to reduce methanogenesis in livestock. Furthermore, the probiotic compositions of the present invention can be used to reduce the number and kind of food-borne pathogens, such as *Escherichia coli* and *Campylobacter jejuni*.

38 Claims, 4 Drawing Sheets

NITRATE- AND NITRITE-REDUCING PROBIOTIC FEED ADDITIVE

CROSS-REFERENCE

The present application claims priority to U.S. Provisional Patent Application Ser. No. 62/204,112 filed Aug. 12, 2015, the content of which is expressly incorporated herein by reference.

BACKGROUND OF THE INVENTION

Field of Invention

The present invention relates to probiotic food additives for livestock, particularly ruminants. Selected strains of a currently unspeciated bacterium of the genus *Paenibacillus* are demonstrated to have increased nitrate- and nitrite-reducing capability compared to wild-type strains and other nitrate-reducing bacteria. Ruminants that have consumed toxic amounts of nitrate, which is converted to nitrite during the digestive process, can suffer from nitrate/nitrite toxicity. Thus, the selected strains can be utilized to reduce nitrate/nitrite toxicity occurring in such animals and be used prophylactically to prevent nitrate/nitrite toxicity in animals consuming high-nitrate diets. As high-nitrate diets have been demonstrated to reduce methane production in the rumen, selected strains of the bacterial species described herein can be used in conjunction with such diets to prevent nitrate/nitrite toxicity while reducing methanogenesis. Furthermore, the bacterial strains can cause reductions in unwanted bacteria and food-borne pathogens, such as *Escherichia coli* and *Campylobacter jejuni*.

Background

Intoxication by nitrates present in forages has been recognized in ruminants for a long time. Nitrates are ubiquitous in feed and water and are essentially nontoxic. However, when nitrates are reduced to nitrites in the rumen, nitrites can be present in deadly concentrations. Nitrates become toxic to ruminants when biologically reduced to nitrite by rumen microorganisms that use nitrate as an anaerobic electron acceptor, thus, nitrites can be present in deadly concentrations in food and water. As nitrate reduction increases, the rate of nitrate reduction to nitrite exceeds the rate of nitrite reduction to ammonia, resulting in accumulation of toxic levels of nitrite. The nitrite produced is rapidly absorbed into the bloodstream where it converts hemoglobin to methemoglobin, resulting in loss of oxygen transporting capacity of the blood, anoxia, and can ultimately result in death by asphyxiation. Currently, nitrate poisons countless cattle every year, creating waste and economic burden on livestock producers.

Several interventions are available to control nitrate/nitrite poisoning, but these are generally limited to inconvenient and labor-intensive animal and plant management strategies. For example, reducing nitrogen fertilization, timing harvest based on precipitation, and use of specific harvesting techniques can reduce the amount of nitrate, but cannot eliminate already-accumulated nitrates. However, silage grown under stressful conditions such as drought conditions can lead to an increased levels of nitrate. Due to the risk of nitrate poisoning, a significant amount of forage is deemed unacceptable for consumption. Hundreds of millions of tons of silage across the United States accumulated high nitrate content during droughts occurring between 2011 and 2012. This led to millions of dollars of loss to the beef and dairy industry. Additionally, it is theorized that the conditions caused by global climate change will be precipitous for high nitrate levels in forage in the future. It is likely, therefore, that the loss of forage and livestock will increase as a result. Thus, the present invention seeks to address this issue by decreasing the potential for nitrate poisoning in ruminants through the use of probiotic nitrate- and nitrite-reducing bacterial strains. The present invention also seeks to address the issue by enabling the consumption of low-quality, high-nitrate feed for efficient usage of available resources.

Avoiding nitrate/nitrite poisoning can also be achieved via animal management strategies. Animal management strategies include feeding practices (e.g., diluting high nitrate feeds with low nitrate feeds, gradually increasing from low to high nitrate feed, and supplementing diets of high nitrate feed with grain). However, young or nutritionally stressed animals may not benefit from such practices. Additionally, these techniques are costly and can result in reduced animal performance, as well as forage health and quantity.

Ruminants that consume a high nitrate diet have been reported to adapt and reduce nitrate to nitrite, and reduce nitrite to ammonia, more rapidly due to selection and induction of microbial nitrate reduction activity. Thus, adding specific nitrate- and nitrite-reducing microorganisms to the diet of livestock, with the intent of altering the nitrite reducing capacity of the gastrointestinal tract microbiome, has long been in practice. Although the mode of action of these direct-fed microbial products and their beneficial effect has not always been scientifically demonstrated, the important role microorganisms play in fermentation and digestion is well recognized. The use of nitrate-respiring *Propionibacterium* species has been described as a direct-fed microbial agent to prevent ruminal nitrate intoxication (see, e.g., U.S. Pat. No. 6,120,810), however, this approach has not gained widespread use due to limitations in the technology. Thus, one aspect of the present invention is to address these technological limitations and provide a bacterial probiotic that can be readily packaged and delivered to livestock, including ruminants.

Methanogenesis is the main route of hydrogen ($H_2$) disposal during the process of rumen fermentation (Beauchemin et al., Aus. J. Exper. Agriculture, (2008) 48:21-27). Removal of $H_2$ from the rumen environment is essential for the efficient continuation of rumen fermentation, but the methane resulting from methanogenesis has been implicated both as a loss of dietary energy to the animal (Johnson and Johnson, J. Anim. Sci., (1995) 73:2483-92) as well as a significant greenhouse gas contributing to global warming (Steinfeld et al., Food and Agriculture Org. of the UN, "Livestock's Long Shadow: Environmental Issues and Options, (2006)). Thus, a solution to both of these problems—efficient conversion of livestock feed to animal production and reducing greenhouse gas emission—would prove both economically and ecologically beneficial.

The production of methane within the digestive tract of ruminants is a sizeable inefficiency. Economically, this energy loss costs the U.S. cattle industry nearly one million dollars a day. Additionally, it is estimated that approximately twenty percent of the powerful greenhouse gas produced each year originates from enteric fermentation, with commercial ruminants being the major source. It is, therefore, an object of the present invention to address the need to reduce methanogenesis in livestock, including ruminants.

The addition of nitrate to the diet of livestock has been demonstrated to reduce methanogenesis (van Zijderveld et al., J. Dairy Sci., (2011) 94:4028-38; Guo et al., J. Anim. Sci., (2009) 22:542-49; Sar et al., J. Anim. Sci., (2005) 83:644-52; Takahashi et al., Anim. Feed Sci. Technol., (1998) 74:273-80; U.S. Pub. No. 2012/0219527; WO 2012/159186). However, the use of nitrate as an alternative hydrogen sink to reduce methanogenesis in the rumen is problematic given that high levels of nitrate in livestock feed can result in nitrate/nitrite poisoning and animal death. Additionally, nitrite accumulation in the rumen can lead to reduced microbial activity in that environment, which leads to reduced feed intake and slower animal growth. Multiple approaches have been taken to alleviate the inhibition of fermentation by nitrite, while also using nitrate to reduce methanogenesis.

Supplementing feed with formate, lactate or fumarate has been suggested (Asanuma et al., J. Dairy Sci., (1999) 82:780-87; Iwamoto et al., Anim. Sci. J., (2001) 72:117-25). Additionally, the co-administration of nitrates with β1-4 galacto-oligosaccharides or nisin (a polycyclic antibacterial polypeptide), has been reported to maintain safe levels of nitrite and methemoglobin while maintaining the beneficial effects of nitrate on methanogenesis (Sar et al., Anim. Feed Sci. Tech., (2004) 115:129-42). However, these chemical additives are not cost effective as they require constant reapplication. Therefore, the strains and methods presented herein provide a mechanism to decrease methanogenesis in livestock using high-nitrate diets, while concomitantly avoiding nitrate/nitrite poisoning in an economical manner.

Enhancement of nitrite reduction in ruminal environments utilizing probiotics has been demonstrated both in vitro and in vivo (Sar et al., (2005) supra; U.S. Pat. No. 6,120,810). A range of bacterial species and combinations of strains has been suggested, including *E. coli, Propionibacterium acidiproprionici*, coryneform bacteria, *Bacillus subtilis, Methylophilus, Actinomyces*, ruminal bacteria and various combinations. However, these bacteria have not come into common usage for several reasons. First, certain species such as *E. coli* are potential human pathogens and are known to cause food-borne illnesses. Thus, the use of such probiotic species is untenable. Second, certain species, such as *P. acidiproprionici*, may actually increase the conversion of nitrate to nitrite faster than normal, exacerbating the toxicity of nitrate-enhanced feeds. Such strains may also be difficult to incorporate into feeds or feed supplements. Thus, one objective of the present invention is to provide a stable probiotic that is economically feasible, non-pathogenic, and effective at preventing or reducing nitrate/nitrite toxicity.

SUMMARY OF THE INVENTION

One aspect of the present invention provides a biologically pure novel strain of a nitrate- and nitrite-reducing bacterium termed strain NRRL 67118.

Also provided herein is a composition for ingestion by a ruminant, comprising a carrier feed composition containing the biologically pure strain NRRL 67118. In some instances, the carrier feed composition is hay, silage, or forage. Particular ruminants for which this feed can be used are cattle, sheep, and goats. In some instances the carrier feed composition also comprises a nitrate salt, such as sodium nitrate, potassium nitrate, calcium nitrate, or ammonium nitrate. In one embodiment, the carrier feed composition is a compound feed. Some compositions of the present invention contain strain NRRL 67118 in an amount from $10^2$ to $10^{20}$ colony forming units per kilogram of dry weight carrier feed.

An additional composition for ingestion by a ruminant is provided and comprises the biologically pure strain NRRL 67118 incorporated into an additive premix or a lick block. A premix or lick block of the present invention can be formulated for ingestion by cattle, sheep and goats. In some instances the additive premix or lick block also contain a nitrate salt, such as sodium nitrate, potassium nitrate, calcium nitrate, or ammonium nitrate. Some premixes and lick blocks of the present invention contain strain NRRL 67118 in an amount from $10^2$ to $10^{20}$ colony forming units per kilogram of dry weight of the premix or lick block.

Several methods are provided herein utilizing strain NRRL 67118. One such method of the present invention involves reducing nitrate/nitrite toxicity in a ruminant by introducing or maintaining a population of strain NRRL 67118 which is capable of anaerobic denitrification of the animal's rumen. In some embodiments, the population is introduced or maintained by feeding the ruminant a carrier feed composition, an additive premix, or a lick block containing the biologically pure strain NRRL 67118. In a particular embodiment, strain NRRL 67118 is present in an amount from $10^2$ to $10^{20}$ colony forming units per kilogram of dry weight of the carrier feed composition, additive premix, or lick block. The population of strain NRRL 67118 can be introduced or maintained in some embodiments by delivering the microbe in an amount of from $10^2$ to $10^{20}$ colony forming units per milliliter of ruminal fluid per day. In a particular embodiment, this feeding occurs for a period of 1 to 10 days. In other embodiments, the microbial population is introduced or maintained by providing the animal a water source containing the biologically pure strain NRRL 67118. In such instances, the strain can be present in the water source at a concentration of from $10^2$ to $10^{20}$ colony forming units per liter.

Further provided herein is a method of preventing nitrate/nitrite toxicity in a ruminant susceptible to such toxicity by introducing or maintaining in population of strain NRRL 67118 which is capable of anaerobic denitrification of the animal's rumen. In some embodiments, the population is introduced or maintained by feeding the ruminant a carrier feed composition, an additive premix, or a lick block containing the biologically pure strain NRRL 67118. In a particular embodiment, strain NRRL 67118 is present in an amount from $10^2$ to $10^{20}$ colony forming units per kilogram of dry weight of the carrier feed composition, additive premix, or lick block. The population of strain NRRL 67118 can be introduced or maintained in some embodiments by delivering the microbe in an amount of from $10^2$ to $10^{20}$ colony forming units per milliliter of ruminal fluid per day. In a particular embodiment, this feeding occurs for a period of 1 to 10 days. In other embodiments, the microbial population is introduced or maintained by providing the animal a water source containing the biologically pure strain NRRL 67118. In such instances, the strain can be present in the water source at a concentration of from $10^2$ to $10^{20}$ colony forming units per liter.

In another embodiment, the invention herein provides a method of reducing gastrointestinal methanogenesis in a ruminant, by administering to the animal a composition comprising an effective amount of a nitrate compound and introduced or maintained in the ruminant's rumen a population of strain NRRL 67118 which is capable of anaerobic denitrification of the rumen. In particular embodiments, the nitrate compound is sodium nitrate, potassium nitrate, calcium nitrate, or ammonium nitrate. The nitrate compound can be present in the compositions of the present invention in an amount of 1 to 100 grams per kilogram of dry weight. In some instances, the microbial population is introduced or maintained by feeding the ruminant a carrier feed composition, an additive premix, or a lick block containing the biologically pure strain NRRL 67118. In particular embodiments, the probiotic strain NRRL 67118 is present in the compositions in an amount from $10^2$ to $10^{20}$ colony forming units per kilogram of dry weight. The ruminal population of strain NRRL 67118 can be introduced or maintained in some embodiments by delivering the microbe in an amount of from $10^2$ to $10^{20}$ colony forming units per milliliter of ruminal fluid per day. In a particular embodiment, this feeding occurs for a period of 1 to 10 days. In other embodiments, the microbial population is introduced or maintained by providing the animal a water source containing the biologically pure strain NRRL 67118. In such instances, the strain can be present in the water source at a concentration of from $10^2$ to $10^{20}$ colony forming units per liter. In some instances, administering a nitrate compound and introducing or maintaining a ruminal population of strain NRRL 67118 occurs concomitantly.

An additional method provided herein involves reducing the numbers of one or more food-borne pathogens in a ruminant by introducing or maintaining a population of strain NRRL 67118 in the animal's rumen which is sufficient to reduce the growth or persistence of the pathogen. As in other embodiments, the population of the probiotic organism can be introduced or maintained by feeding the ruminant a carrier feed composition, an additive premix, or a lick block containing the biologically pure strain NRRL 67118. In a particular example, strain NRRL 67118 is present in an amount from $10^2$ to $10^{20}$ colony forming units per kilogram of dry weight of the carrier feed composition, additive premix, or lick block. Specific organisms which can be reduced in a ruminant include *E. coli* and *C. jejuni*.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

STATEMENT OF DEPOSIT

Figure 1:
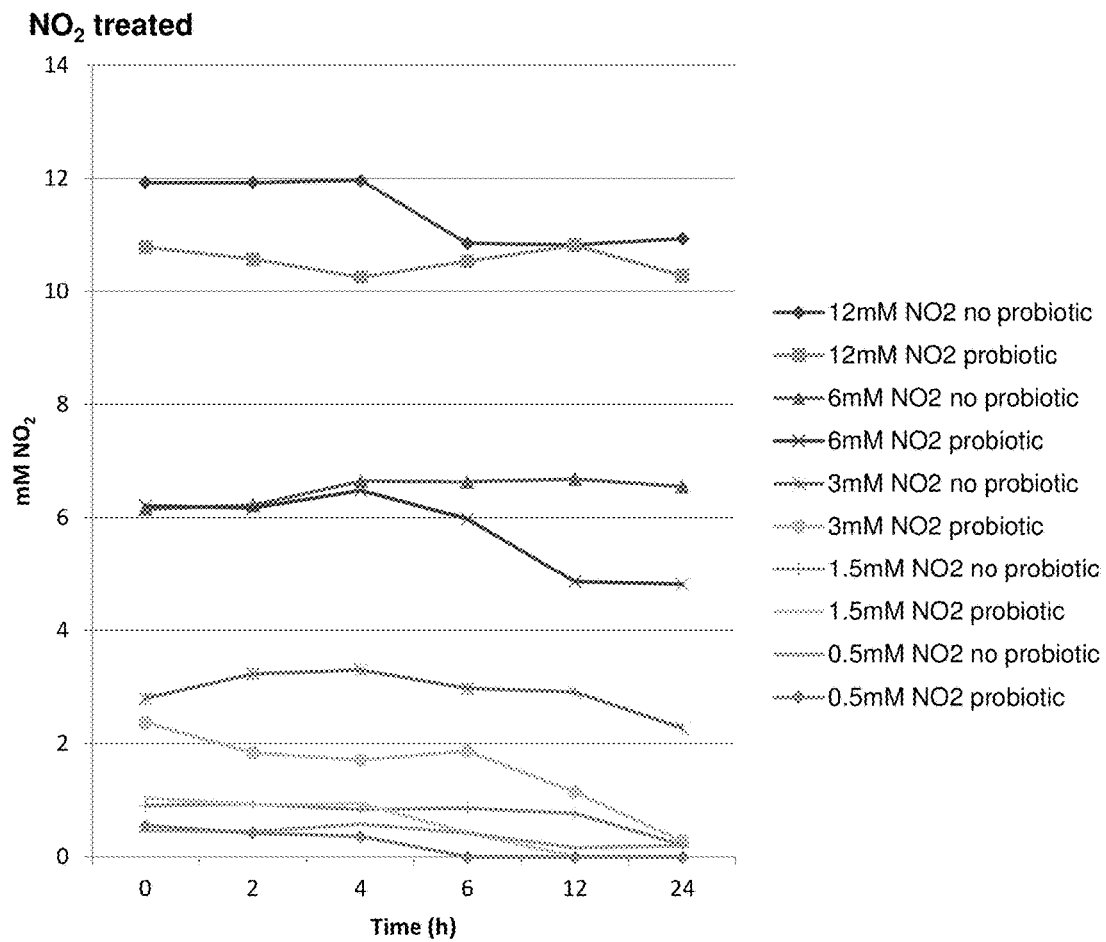
FIG. 1 provides a graph showing the effects on nitrite reduction in vitro in cultures supplemented or not with strain NRRL 67118.

A strain representative of the inventions disclosed herein was deposited on Aug. 14, 2015 under the terms of the Budapest Treaty with the Agricultural Research Service (ARS) Patent Culture Collection. A representative *Paenibacillus* sp strain was deposited under ARS Patent Culture Collection Reference No. NRRL 67118. The microorganism deposit was made under the provisions of the "Budapest Treaty on the International Recognition of the Deposit of Microorganisms for the Purposes of Patent Procedure". All restrictions on the availability to the public of these deposited microorganisms will be irrevocably removed upon issuance of a United States patent based on this application. For the purposes of this invention, any *Paenibacillus* sp strain having the identifying characteristics of NRRL 67118, including subcultures and variants thereof which have the identifying characteristics and activity as described herein are included.

DETAILED DESCRIPTION OF THE INVENTION

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

Use of the terms "a" and "an" include the possibility that more than one of the element is present, unless the context clearly requires that there be one and only one of the elements. The indefinite article "a" or "an" thus usually means "at least one".

As used, herein the terms "probiotic" and "probiotic composition" refer to an additive premix, or compound feed, containing the bacterial strains of the present invention, usually, but not necessarily in combination with other components. A probiotic or supplement can be added to an animal's feed or ration to form a supplemented feed in accordance with the present invention. Typically, the probiotic of the present invention is in the form of an ingestible solid when added to animal feed, or as a dissolvable formulation when added to water or other liquid dietary components. In practice, a probiotic of the present invention can be applied to an animal's gastrointestinal tract by providing it in food or water. Alternately, a probiotic can be used as a component of products intended for ingestion by animals, such as compound animal feeds or lick blocks. A probiotic can be applied to an animal in any amount necessary to achieve desired goals, e.g., prevention of nitrate/nitrite poisoning, treatment of nitrate/nitrite poisoning, treatment of methemoglobinemia, and decrease of methanogenesis. Accordingly, an animal can be fed a probiotic containing a bacterial strain of the present invention in any amount, for example ranging from $1.0 \times 10^3$-$1.0 \times 10^{20}$ cfu/kg dry weight of feed stuff.

The term "probiotic microorganism" (and variations thereof) refers to a microorganism found in a probiotic of the present invention and intended for delivery to the gastrointestinal tract of a target animal.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g.

In some aspects of the present invention, a probiotic will be fed to a ruminant. Taxonomically, a ruminant is a mammal of the order Artiodactyla that ferments plant-based food within a first stomach (the rumen) and then regurgitating the semi-digested mass (the cud) and chewing it again. Rumination is the process of rechewing the cud to stimulate digestion by breaking down plant matter further. There are roughly one hundred and fifty species of ruminants, including both wild and domestic species. Non-limiting examples include alpacas, antelope, bison, buffalo, camels, cattle, deer, giraffes, goats, sheep, water buffalo, wildebeest, and yaks. The present invention is primarily concerned with domesticated ruminants, especially those held for commercial livestock breeding. Thus, in some preferred embodiments of the invention, cattle, goats, and sheep are fed a probiotic of the present invention.

Some embodiments of the present invention comprise the feeding of a bacterial strain to a target animal, where the strain is capable of reducing nitrate and nitrite in the gastrointestinal tract of the animal. Typically, the reduction of nitrate and nitrite occurs in the rumen, when the probiotic is fed to a ruminant. However, nitrate and nitrite reduction can occur in any portion of the gastrointestinal tract of the target animal where the bacterial strain can survive.

Bacterial Strain Characteristics/Amounts

In most embodiments of the present invention, a probiotic composition contains a microbe with nitrate- and nitrite-reducing capabilities. Typically, nitrite accumulating in the gastrointestinal tract of an animal is reduced to ammonium by a microbial strain or species useful in the present invention. In instances where a probiotic composition of the present invention comprises only a single microorganism, the microorganism typically contains certain preferred phenotypic and biochemical characteristics. In some embodiments, the organism is a spore-forming organism. Spores are a resilient morphological form and can facilitate the organism being packaged, exhibiting a long shelf-life, remaining viable when incorporated into compound feeds or lick blocks, and other aspects that affect economic viability for use as a probiotic. Additionally, a preferred microorganism useful as a probiotic in the present invention is capable of growth both aerobically and anaerobically. Still another preferred characteristic is that a probiotic microbe for use in the inventions disclosed here is non-pathogenic in the target animals, and is also non-pathogenic in humans. In some instances, a probiotic microorganism inhibits other potentially harmful food-borne pathogens such as *E. coli* and *C. jejuni*. In the most preferred embodiments, a probiotic microbe has both nitrate-reducing and nitrite-reducing biochemical capabilities. In a specific embodiment, the probiotic microbe used to practice the invention described herein is the unspeciated bacterium described herein termed strain NRRL 67118.

In some embodiments, a probiotic composition comprises more than one microbial strain or species. For instance, a probiotic composition can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more individual species or strains of microbe. Thus, a probiotic composition of the present invention can comprise one or more strains of the same microbial species, one or more microbial species, or a combination thereof. Many examples of such microbes producing nitrate or nitrite reductase activity are known in the art including, but not limited to species and strains within the groups or genera *Achromobacter*, *Actinomyces* (e.g., *Streptomyces coelicolor*), *Bacillus* (e.g., *B. subtilis*), coryneform bacteria (e.g., *Corynebacterium glutanicum*), *Escherichia* (e.g., *E. coli*), *Megasphaera*, *Methylobacillus*, *Methylomonas*, *Methylophilus*, *Paenibacillus*, *Propionibacterium* (e.g., *P. acidiproprionici*), *Protaminobacter*, *Pseudomonads*, *Pyrobaculum*, *Salmonella*, *Selenomonas*, *Shigella*, *Veillonella*, and *Wolinella*. In preferred embodiments, no probiotic microbe used in a composition of the present invention will be pathogenic in either the host animal or humans. In a particular embodiment, one of the microbes utilized in a probiotic composition with more than one strain or species of microbe is the unspeciated bacterium termed strain NRRL 67118.

In some embodiments, a probiotic composition of the present invention comprises a nitrate and/or nitrite reducing microbe in an amount of $10^2$ to $10^{20}$ cfu/kg, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/kg, on a dry weight basis. Colony-forming unit (CFU) is a measure of microbial numbers that refers to viable cells. CFU can be determined using any means known in the art appropriate for the microbe of interest, such as by growing a diluted sample on an agar or trypticase soy agar plates and counting colonies after incubation.

In other embodiments, a probiotic composition of the present invention is fed to a target animal in order to achieve a particular number of a nitrate- and nitrite-reducing microbes in a gastrointestinal environment such as the rumen. For example, the amount of the probiotic microbe can be formulated to deliver from $10^2$ to $10^{20}$ cfu/ml ruminal fluid, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/ml ruminal fluid. One of skill in the art can utilize any methodology known to adjust the raw number of microbes in a given dosage of probiotic composition based on ruminal volume of the target animal.

Delivery of a probiotic composition of the present invention can occur over any appropriate timeframe. For example, an animal can be fed once, twice, thrice, or more times daily with a probiotic described herein, or can be provided ad libitum access to a probiotic. A dosing regimen can last for 1, 2, 3, 4, 5, 6, 7, 8, 9, 0, 11, 12, 13, 14, 15, 16, 17, 18, 19, 20, 21, 22, 23, 24, 25, 26, 27, 28, 29, 30, or more days. The dosing regimen can be altered according to need. Thus, dosing with a probiotic composition can be intermittent (e.g., weekly, monthly, bi-monthly, random, etc.), or continuous. Dosing can be performed a single time, or multiple times. Dosing can be performed when animals are fed high nitrate diets, such as nitrate-supplemented feeds or naturally high-nitrate feeds. Dosing with a probiotic composition of the present invention can be performed when an animal is known or suspected of suffering from nitrite poisoning or methemoglobinemia. One of skill in the art is capable of choosing a dosing regimen according to need or desired result.

Form of Probiotic

Dosing of an animal with a probiotic composition of the present invention can be achieved by incorporating the composition into the diet of a target animal, for example, mixed into compound animal feeds, added as a premix to fodder or silage, dissolved in drinking water, incorporated into salt or other lick blocks, or using any other methodology known in the art. The mechanism of delivery to the gastrointestinal tract, particularly the rumen, is well within the skill of one in the art to decide based on both the diet and anatomy of the target animal.

In general, probiotic compositions of the present invention containing nitrate- and nitrite-reducing microbes are intended to decrease nitrite poisoning via an in vivo process, typically within the rumen of a target animal. Thus, in most embodiments, a probiotic composition is delivered to an animal's gastrointestinal tract. One such delivery mechanism is by including the probiotic composition in feeds for animals. Any feed appropriate for a target animal can be utilized, non-limiting examples include grasses, cereals, oilseed cakes, vegetative wastes and starches. Such supplemented feeds can also contain vitamins, trace nutrients, mineral salts, fats, binders or any other desired additive known in the art. Additional supplements can be chosen for inclusion in probiotic-supplemented feeds, but preferably will not impede the growth or nitrate-/nitrite-reducing capacity of a probiotic microbe.

"Compound feed" is fodder that is blended from various raw materials and additives. Such blends can be formulated according to the specific requirements of the target animal. The main ingredients used in commercially prepared compound feeds typically include wheat bran, rice bran, corn meal, cereal grains, such as barley, wheat, rye and oat, soybean meal, alfalfa meal, wheat powder and the like. A compound feed can comprise crude protein and digestible total nutrients in appropriate concentration, although the invention is not particularly limited in this respect. In practice, livestock can be fed a combination of compound feed and silage, hay, or other non-compound feeds. It is within the skills of one trained in the art to determine proper amounts of components to be included in an animal diet. In some instances, compound feeds are manufactured to include a probiotic of the present invention.

Compound feeds including a probiotic of the present invention can be of any physical form appropriate for delivery to a target animal. Non-limiting examples include granules, capsules, pellets, kibbles, powders, liquids, semi-liquids or gels. Additionally, a probiotic composition can be added to a non-compound feed (e.g. silage, forage, etc.), for example as a powder or granules.

Probiotics of the present invention can also be included in premixes. Premixes can be included directly into compound feeds, or can be prepared separately for addition to any animal feed, silage, forage, or supplement. Premixes can contain any desired ingredients in addition to probiotics of the present invention. For example, a premix can contain micro-ingredients such as vitamins, minerals, salts chemical preservatives, antibiotics, fermentation products, and other essential or desired ingredients. In some preferred embodiments, a premix contains both nitrate and a probiotic microorganism.

Probiotic compositions of the present invention can also be presented to target animals in the form of veterinary compositions, preferably in a digestible carrier. Veterinary compositions including a probiotic composition of the present invention can be given with, or separately from, feeds and can be given prophylactically, or for treatment of a diagnosed or suspected condition (e.g., nitrite poisoning). Veterinary compositions can be of any appropriate form known in the art including, but not limited to, pills, capsules, pellets, liquids, semi-liquids, gels, etc. Such veterinary compositions may be formulated to deliver from $10^2$ to $10^{20}$ cfu/ml ruminal fluid, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/ml ruminal fluid/animal/day.

The probiotics of the present invention may also be presented in the form of lick blocks (e.g., lick-sticks or lick-stones). Lick blocks of the present invention can take any form known in the art as the actual shape of the lick block is not integral to the practicing the invention. In addition to the nitrate- and nitrite-reducing microbe lick blocks can comprise other additives such as nitrate salts, trace nutrients, vitamins, mineral salts, sulphate salts, proteins, carbohydrates, sulphur, sulphides, glucide carriers, aromatising and other sensory additives, and various types of binders, including, but not limited to, cements, gypsum, lime, calcium phosphate, hydroxide and carbonate, magnesium sulphate, oxide and hydroxide, aluminium sulphate, alum and gelatin. Any such form known or developed in the art can be utilized to provide a target animal with a probiotic of the present invention and the exact form and composition is not integral to practicing the inventions disclosed herein. In one embodiment, a lick block of the present invention comprises both a nitrate source and a probiotic microorganism capable of reducing nitrate and nitrite.

In some embodiments a probiotic composition of the present invention can be applied to the skin or hide of an animal. Such topical applications can be formulated as dry, liquid, or semi-liquid sprays, powders, ointments, gels or any other appropriate topical formulation.

Other Components

In some embodiments, a nitrate- and nitrite-reducing probiotic microorganism of the present invention is provided to an animal of interest in combination with a nitrate compound. The combination of microorganism and nitrate compound will typically be formulated as a solid, liquid or semi-liquid premix, compound feed, or lick block. The amount of nitrate compound in such formulations can be in any amount desired, for example, nitrate can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more grams per kilogram on a dry weight basis. Typically, the amount of nitrate present in a premix or lick block formulation will comprise less than 500 g/kg nitrate, less than 475 g/kg, less than 450 g/kg, less than 425 g/kg, less than 400 g/kg, less than 375 g/kg, less than 350 g/kg, less than 325 g/kg, less than 300 g/kg, less than 275 g/kg, less than 250 g/kg, less than 225 g/kg, less than 200 g/kg, less than 175 g/kg, or less than 150 g/kg nitrate on a dry weight basis. One of skill in the art can readily determine the amount of nitrate to be included in a premix or lick block based on multiple factors, such as the type of animal and the amount of nitrate already present in the animals' diets. These amounts of nitrate can be used in any combination with a probiotic microbe present in an amount of $10^2$ to $10^{20}$ cfu/kg, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/kg, on a dry weight basis.

Nitrate compounds useful in practicing certain embodiments of the present invention are typically a physiologically acceptable or tolerated nitrate or nitro compound. Useful compounds will typically be ones that are readily available for reduction in the gastrointestinal tract of an animal, particularly in the rumen. In most instances a useful nitrate compound will be soluble in water or ruminal fluid. Thus, a nitrate compound preferably comprises an ionic form of nitrate, for example an inorganic nitrate salt such as sodium nitrate, potassium nitrate, calcium nitrate, or ammonium nitrate. Additionally, nitro compounds (organic molecules containing one or more nitro groups) can be utilized in addition to, or in lieu of inorganic nitrate salts. Non-limiting examples of nitro compounds, include 2-nitropropanol, nitroethane and nitroethanol. These compounds can be utilized singly, or in combination, to achieve a desired nitrate composition. These compounds are provided by way of example only and are not limiting on the practice of the present invention.

Nitrate can also be provided along with a probiotic organism of the present invention in the form of high-nitrate silage, hay, forage, and the like. Typically, stressed plants have higher nitrate levels than non-stressed plants. For example, hay grown under drought (i.e., stress) conditions can have many-fold increased concentration of nitrates compared to hay grown under non-drought conditions. Thus, probiotic microbes of the present invention can be added to the diet of livestock ingesting such plants, thereby providing both increased nitrate and the microorganisms of the present invention.

Probiotic compositions of the present invention can comprise any additional ingredient desired. Such components can include additives intended to improve the quality of feed and increase animal performance, such as vitamins and micronutrients. Compositions of the present invention can also or alternately comprise carriers, excipients, fillers, binders, salts and the like. Non-limiting examples of additional components include lactose, mannitol, crystalline cellulose, starch, sucrose, sodium salts, sulfate salts, potassium salts, magnesium salts, manganese salts, sodium hydrogen carbonate, gum arabic, gum tragacanth, sodium alginate, cellulose derivatives, PVP, vitamins, amino acids, trace elements, microbial stabilizers, and digestibility enhancers.

Additionally, any feed additive known to those of skill in the art can be utilized in the practice of the present invention. Such compositions include, but are not limited to, emulsifiers, preservatives, antioxidants, stabilizing agents, acidity regulators, silage additives, natural and artificial flavors, natural and artificial colorants, natural and artificial odorants, and antibiotics. It will be clear to one of skill in the art that these components are not an exhaustive list of additional ingredients that can be included in probiotic compositions of the present invention without departing from the invention.

Methods of Use

Probiotic compositions of the present invention can be utilized in multiple ways. As described herein. Probiotic microorganisms can be utilized alone, or in combination with one or more nitrate compounds. In both instances, other components as described previously can also be included in any premix, compound feed, block lick, dietary supplement or veterinary composition.

Methane production is a naturally-occurring process in healthy animals, including ruminants, that neither enhances nor decreases an animal's general health. However, excess methane production can decrease animal performance and limit efficiency of nutrient utilization. Thus, decreasing methanogenesis can result in an increase in animal growth and productivity, providing economic benefits. Furthermore, because of the potent greenhouse effects of methane, decreasing methanogenesis in livestock can result in positive environmental impact.

In one aspect of the present invention, a method of reducing ruminal methanogenesis is provided. In general, such methods comprise administering an effective amount of a combination of nitrate compound and a nitrate- and nitrite-reducing probiotic microbe to an animal. "Effective amount" in this context refers to a sufficient amount of nitrate to cause a reduction in methanogenesis and a sufficient amount of probiotic microbe to prevent or address nitrate/nitrite toxicity. "Reducing methanogenesis" refers to a reduction of the production of methane gas by a target animal, typically by reducing methane gas production in the gastrointestinal tract, especially the rumen. Fermentation in the rumen and other parts of the gastrointestinal tract by methanogens is the most common route of methanogenesis in ruminants. Nitrate is an alternate hydrogen sink that can be utilized to reduce conversion of hydrogen into methane. However, as described herein, excess nitrate in the diet of an animal can lead to nitrate/nitrite poisoning. Thus, the present invention addresses both of these issues concomitantly by combining the hydrogen sink properties of excess nitrate with the nitrate/nitrite reducing capabilities of a probiotic microbe of the present invention.

In some embodiments of the present invention, reducing methanogenesis is achieved by feeding an animal a diet comprising both a nitrate source and a probiotic microbe. Typically, nitrate will be fed to an animal in an amount between 0.1-10 g/kg body weight per day, for example 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, or more g/kg nitrate per day. A probiotic microbe can be applied to an animal so as to deliver from $10^2$ to $10^{20}$ cfu/ml ruminal fluid, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/ml ruminal fluid/animal/day. The nitrate compound and the nitrate- and nitrite-reducing probiotic microbe can be applied to the animal in a single mix, concomitantly but separately, overlapping, or completely non-concomitantly.

One of skill in the art will recognize that the dosages defined herein as g/kg/day and cfu/ml ruminal fluid/day represent an average amount of the respective components given during a period of time (e.g., during a week or a month of treatment). The nitrate and/or probiotic can be administered on any schedule, for example every day, every other day, every other two days, etc., without departing from the methods of the present invention. In some embodiments, daily administration of both a nitrate compound and a probiotic microorganism is preferred. Such daily dosages can be applied to the animal during feeding. Nitrate compounds and probiotic microbes can also be provided on alternate days or weeks. The methods of the present invention do not require that the application of the nitrate compounds and/or the probiotic compounds be continuous during the treatment period.

Utilizing the methods provided herein, methane production in a treated animal can be reduced by 0.5-10 grams of methane per kilogram of feed, for example. 0.5, 1.0, 1.5, 2.0, 2.5, 3.0, 3.5, 4.0, 4.5, 5.0, 5.5, 6.0, 6.5, 7.0, 7.5, 8.0, 8.5, 9.0. 9.5, 10.0 or more g methane/kg feed. One of skill in the art will recognize that such production, and therefore reduction of methane production, occurs over time as digestion occurs. One of skill in the art will recognize that there are other ways to determine amounts of methane produced, for example liters per day per animal, megacalories per day per animal, moles per day per animal, volume or mass of methane per set volume of ruminal fluid or ruminal volume, and other methodologies. The methods presented herein result in a percent decrease in methane produced per animal provided with a nitrate compound and a probiotic microorganism of the present invention, regardless of the measurement utilized to determine methane production. A decrease in methane production can be between 1% and 50%, for example 1%, 5%, 10%, 15%, 20%, 25%, 30%, 35%, 40%, 45%, 50%, 55%, 60%, 65%, 70%, 75%, 80%, 85%, 90%, 95%, 100% or any percentile within that range.

In another embodiment of the present invention, a method is provided to decrease nitrate/nitrite toxicity, including methemoglobinemia, in a target animal. Additionally, a method is provided to prevent nitrate/nitrite toxicity in animals consuming high-nitrate diets. Rumen microflora reduce nitrate to nitrite and then reduce nitrite to ammonia. In instances where nitrate intake is high, excess nitrite can accumulate as the reduction of nitrite to ammonia is typically a slower process than the reduction of nitrate to nitrite. As explained above, this can lead to an accumulation of nitrite in the rumen. Nitrite is readily absorbed across the rumen wall and enters the circulatory system, where it converts hemoglobin from the ferrous form to the ferric form, methemoglobin. Methemoglobin is incapable of transporting oxygen, thus can result in anoxia in the animal. The level of anoxia can vary, resulting in depressed animal performance in mild cases to animal death in severe cases. As mentioned above, expensive or time-intensive methods of animal care, especially altering diets to low-nitrate feeds can address this issue. However, such methodologies lead to wasted resources (e.g., silage, hay, forage and the like that contain high nitrates) and do not prevent reoccurrence of nitrite poisoning.

In general, a method provided herein to prevent nitrate/nitrite toxicity comprises providing a target animal on a high-nitrate diet with a nitrate- and nitrite-reducing probiotic microbe of the present invention. As used herein, the terms "high-nitrate diet" and "high-nitrate feed" include those diets or feeds that would result in nitrate toxicity in the absence of a probiotic microbe of the present invention. In general, the present invention provides a method of applying a nitrate- and nitrite-reducing probiotic microbe to an animal prior to, or concomitantly with, providing the animal with a high-nitrate diet or feed. In one embodiment, a probiotic microorganism is provided to the animal days, weeks, or months prior to ingestion of a high-nitrate diet. A probiotic organism can be applied to an animal with each feeding, once daily, twice daily, once weekly, bi-weekly, monthly, or on any other schedule. Such application schedules are readily determined by one of skill in the art and modified based on any relevant factors, such as the type of animal or the level of dietary nitrate. The amount of the microbe provided can also be varied as described above. Any method of application to a target animal in which the probiotic microbe reaches the gastrointestinal tract, and more typically, the rumen, can be utilized.

In an alternate embodiment, the probiotic microbe is provided to the animal at the same time the animal is ingesting a high-nitrate diet. High-nitrate diets can consist of any animal foodstuff, including but not limited to forage, hay, silage and compound feeds as well as nitrate-containing water sources. Nitrates can be naturally occurring in the animal's diet, or can be present as a dietary supplement. In general, a probiotic composition comprising one or more microorganisms is applied to an animal so as to alter the gastrointestinal microflora, especially the ruminal microflora, so that it is capable of reducing both nitrate and nitrite efficiently. A probiotic organism can be applied to an animal with each feeding, once daily, twice daily, once weekly, bi-weekly, monthly, or on any other schedule. Such application schedules are readily determined by one of skill in the art and modified based on any relevant factors, such as the type of animal or the level of dietary nitrate. The amount of the microbe provided can also be varied as described above. Any method of application to a target animal in which the probiotic microbe reaches the gastrointestinal tract, and more typically, the rumen, can be utilized.

Whether applied to an animal prior to its beginning a high-nitrate diet, or applied concomitantly with a high-nitrate diet, the method of the present invention comprises providing a probiotic composition to the animal so as to achieve a probiotic microbe in the amount of $10^2$ to $10^{20}$ cfu/ml ruminal fluid, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/ml ruminal fluid. One of skill in the art will recognize that these cfu numbers can refer to the numbers achieved for an individual microbe of a probiotic composition comprising more than one microbe, or can refer to the total number of all microbial strains in a particular probiotic composition.

Another method of the present invention provides for an increase in the nitrite-reduction capacity of a target animal by applying a probiotic composition of the present invention to the animal, allowing the one or more nitrite-reducing microbial strains of the composition to colonize the animal, thereby increasing nitrite-reducing capacity. This method preferably results in an increase in nitrite reducing capability of the microflora of the animal's gastrointestinal tract, especially the ruminal microflora. Changes brought about to an animal's microflora can be transient, lasting days, weeks, months or years. Alternately, changes in the microflora can be permanent where the probiotic composition provides one or more species or strains of microbe that colonize the gastrointestinal tract. A probiotic composition utilized to increase nitrite reduction capability of a target animal can result in any of the target ranges of microbial concentrations described above. In preferred embodiments, a probiotic composition is applied to an animal such that the one or more microbes therein reach the gastrointestinal site of interest, especially the rumen.

An additional method of the present invention provides for a reduction in the numbers of food-borne human pathogens in a target animal by applying a probiotic composition described herein. In some embodiments, the one or more microbes of a probiotic composition have the capability of decreasing the number of food-borne pathogens present in the gastrointestinal tract. Decrease in the number of such organisms can refer to a reduction in the absolute numbers present of an individual strain or species, as well as a decrease in the number of individual pathogenic species or strains present. Such decrease can be achieved via competition, via the production of anti-microbial substances by the probiotic microbes, a combination of these two, or any other mechanism. The methods of the present invention can produce a decrease in viable food-borne pathogenic organisms, such as a decrease of $10^2$ to $10^{10}$ cfu/ml ruminal fluid, for example $10^2$, $10^3$, $10^4$, $10^5$, $10^6$, $10^7$, $10^8$, $10^9$, $10^{10}$, or more cfu/ml ruminal fluid. In particular embodiments, applying a probiotic microbe of the present invention to a target animal decreases the numbers of *E. coli*, *C. jejuni*, or both present in the gastrointestinal tract of the animal.

Water Reclamation and Treatment

Another aspect of the present invention utilizes strain NRRL 67118 not in animals, but in water to alleviate nitrate and nitrite contamination. In general, this method involves adding a sufficient amount of strain NRRL 67118 to a body of water containing undesirably high levels of nitrate or nitrite in order to allow for the reduction of nitrate and nitrite to more desirable byproducts.

Preferably a NRRL 67118 culture is added to the water in the form of a water treatment composition. The water treatment composition can be formulated as a solid, a liquid or a semi-liquid. Solid and/or dry formulations will typically comprise spores of NRRL 67118. Liquid and semi-liquid formulations can comprise spores, live cultures, or both. Additional components, for example, antibacterials, inorganic salts, micro- and macro-nutrients, or any other desired component that preferably does not interfere with growth of, or nitrate- and nitrite-reducing capabilities of, strain NRRL 67118 can be added to any formulation of the invention.

The body of water treated can be naturally occurring or man-made, including water tanks, ponds, rivers, reservoirs and water treatment reservoirs. As strain NRRL 67118 is capable of aerobic and anaerobic growth, nitrate- and nitrite-reducing biochemical activity can occur in oxygenated and un-oxygenated water. For smaller volume bodies of water, strain NRRL 67118 can be added in amounts ranging from $10^2$ to $10^{20}$ cfu/ml liter, for example $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/liter. For larger bodies of water, preferably $10^{10}$ to $10^{20}$ organisms are added per surface acre of the body of water, for example $10^{10}$, $10^{11}$, $10^{12}$, $10^{13}$, $10^{14}$, $10^{15}$, $10^{16}$, $10^{17}$, $10^{18}$, $10^{19}$, $10^{20}$ or more cfu/surface acre. One of skill in the art will recognize that multiple environmental factors can alter the growth and persistence of strain NRRL 67118 in treated water. Thus, reapplication of the bacteria is required under some circumstances.

Addition of strain NRRL 67118 to such water sources can result in a decrease in the percentage of nitrate and nitrite in a given body of water. Additionally, alleviating nitrate or nitrite contamination utilizing the methodology of the present invention can also occur where nitrate and nitrite levels do not appreciably change, but the body of water receives additional nitrates and nitrites (such as from agricultural run-off) following treatment.

The invention as defined here above will be illustrated and explained in more detail in the following experimental part, which is not intended to limit the scope of the invention in any way.

EXAMPLES

Example 1

Strain Isolation and Phenotypic Characterization

Ruminal fluid was collected from a fistulated cow and strained though two layers of cheese cloth. The ruminal fluid was distributed under anaerobic conditions in triplicate to crimp-top tubes with medium B with 36 mM $NaNO_3$ and a gas phase of 50:50 $H_2$:$CO_2$. This concentration was chosen to approximate ruminal nitrate concentrations under nitrate toxicity. Culture tubes were incubated without agitation at 39° C. Medium B contains (mg/100 ml): $K_2HPO_4$ 22.5; $KH_2PO_4$, 22.5; $(NH_4)_2SO_4$, 45; NaCl, 45; $MgSO_4 7H_2O$, 4.5; $CaCl_2$, 2.25; thiamine, 0.2; pantothenate, 0.2; nicotinamide, 0.2; pyridoxine-HCl, 0.2; riboflavin, 0.2; p-aminobenzoic acid, 0.1; biotin, 0.0005; folic acid, 0.005; lipoic acid, 0.005; lipoic acid, 0.005; vitamin B-12, 0.002; resazurin, 0.1; cysteine-HCl, 50; $Na_2CO_3$, 400; phytone peptone, 800; and clarified rumen fluid at 8% vol/vol. Cysteine-HCl and $Na_2CO_3$ were added after the pH of the medium containing the other ingredients was adjusted to 6.8. After three 24 h consecutive batch cultures samples were heated for 10 min at 100° C. to eliminate all non-spore formers. Cultures were then diluted to $10^{-5}$ and plated on medium B with 36 mM $NaNO_3$ and 2% agar. Colormetric nitrite detection overlay methodology was employed to pick colonies with $NO_3$ reduction capacity according to previously described methods. (Glaser & DeMoss, J. Bacteriol., (1971) 108:854-60).

The medium used to test the effects of spore-forming probiotic strains on $NO_3$ and $NO_2$ reduction contained (mg/100 ml): 40% clarified ruminal fluid using 100% $CO_2$ as the anaerobic gas phase. Cultures were inoculated with overnight grown cultures of probiotic strains and 10% vol/vol of fresh rumen fluid. Culture fluid samples were collected at 0, 2, 4, 6, 12, and 24 h for colorimetric determination of $NO_2$ and $NO_3$ concentration and 0 and 24 h for gas chromatographic analysis of $CO_2$, $H_2$, and $CH_4$ and volatile fatty acids.

After nitrate and nitrite selection via three 24 h consecutive batch cultures samples and nitrite detection overlay, individual strains were selected for further $NO_2$ reductive capacity. Individual strains were grown in Medium B with 3 mM, 6 mM, and 12 mM $NaNO_2$ successively. Optical density and colorimetric determination of $NO_2$ reduction were used to monitor for strains with the greatest $NO_2$ reductive capacity. Strain NRRL 67118 surpassed the other strains in terms of growth density, growth rate, and $NO_2$ removal. Table 1 shows a comparison of "WT 97-R4" which is the naturally-occurring strain of an unspeciated bacterium with "strain NRRL 67118" which is a mutant strain of this unspeciated bacterium of the genus *Paenibacillus* isolated following nitrate and nitrite selection. Cultures were grown in medium B with 6 mM NO2 at 39° C. for 24 h. As can be seen, the two strains differ markedly in biomass, specific growth rate and nitrite removal.

TABLE 1

Comparison of wild-type and mutant strains of a novel unspeciated bacterium.

| Isolate | $OD_{max}$ (OD600) | $\mu_{max}$ ($hr^{-1}$) | $NO_2$ removal$_{max}$ (mM $hr^{-1}$) |
|---|---|---|---|
| "WT 97-R4" | 0.279 ± 0.02 | 0.026 | 2.235 ± 0.12 |
| "Strain NRRL 67118" | 0.545 ± 0.03 | 0.075 | 5.85 ± 1.00 |

To determine whether $NO_2$ reduction capacity of strain NRRL 67118 was a stable or transient ability, cultures of the strain were grown in the presence or absence of high nitrite. Cultures were grown in three successive 24 hr cultures of Medium B with no additional nitrite added or 6 mM $NaNO_2$. The results (Table 2) demonstrate that the nitrate/nitrite reducing capacity of strain NRRL 67118 does not change when the initial selective pressure of high nitrate/nitrite is removed. These phenotypes thus appear to represent a stable genetic alteration of the NRRL 67118 strain compared to wild-type microflora (e.g., "WT 97-R4").

TABLE 2

Assessment of Nitrite Reduction capability stability.

| Medium B with: | Reduction of NO$_2$ after 24 h incubation of pre-exposed cells | Std Dev | Reduction of NO$_2$ after 24 h incubation of non-exposed cells | Std Dev |
|---|---|---|---|---|
| NO$_3$ | 92% | 3.7 | 87% | 1.9 |
| NO$_2$ | 45% | 10.7 | 52% | 19.5 |

Spore-formation was tested via the addition of 100% ethanol at 70% vol/vol for 10 minutes under agitation then plated on spore selecting plates (Egg yolk agar) and grown at 39° C. either aerobically or anaerobically. The results—reported as mean number of colonies (CFU/ml) in Table 3—demonstrate that strain NRRL 67118 is capable of sporulation and germination under aerobic and anaerobic conditions.

TABLE 3

Analysis of sporulation capability of strain NRRL 67118.

| | Ethanol treatment | |
|---|---|---|
| Media previously grown on | Plated aerobic | Plated anaerobic |
| TSB anaerobic | 100 | 120 |
| Medium B with NO$_2$ anaerobic | 100 | 250 |
| TSB aerobic | TNTC | TNTC |
| Medium B with NO$_2$ aerobic | TNTC | TNTC |

To determine whether Strain NRRL 67118 demonstrated anti-microbial capabilities, co-culture experiments were performed studying two representative food-borne bacterial pathogens. Tubes were inoculated (0.2% vol/vol) with *E. coli* O157:H7 in the first experiment or *C. jejuni* in the second experiment and the respective co-culture strain NRRL 67118 (0.2% vol/vol) in triplicate. The pure- and co-culture tubes were closed and incubated upright without agitation at 39° C. Fluids from pure and co-cultures were collected and plated in triplicate at 0, 6, 24 and 48 h for viable cell count enumeration. Log transformations of cfu/ml of *E. coli* and *C. jejuni* were tested for treatment effects at each sample time by a general analysis of variance. A 2 to 3 log$^{10}$ CFU reduction in the growth of both *E. coli* and *C. jejuni* was observed (Table 4).

TABLE 4

Inhibition of growth of *E. coli* and *C. jejuni* by strain NRRL 67118.

| | *E. coli* NO$_3$ addition anaerobically | no NO$_3$ aerobically | *C. jejuni* no NO$_3$ aerobically |
|---|---|---|---|
| Pathogen | 7.69 | 9.04 | 8.77 |
| Pathogen + NRRL 67118 | 5.73 | 7.00 | 6.74 |

Example 2

Genetic Analysis

Initial indications from phenotypic, cell morphology and colony morphology analyses suggested that this bacterial strain was a member of the genus *Paenibacillus*. To determine whether this was indeed the case, genetic analysis of the genome of this organism was performed. DNA from pure cultures of strain NRRL 67118 was extracted using Qiagen DNA extraction stool kits. Sequencing was performed using Illumina MiSeq and analyzed using CLC genomic workbench.

Based on preliminary annotation, the presence of genes conferring nitrite and nitrate reducing capacity as well as denitrifying capacity was confirmed in strain NRRL 67118 (Table 5). It has been corroborated to be a spore former with no motility. The largest contigs only blasted to *Paenibacillus* at ~84% identity (while the 16s gene was at 95%). This suggests that it is less similar to the genera *Paenibacillus* than previously thought, and likely represents a member of a new genus.

TABLE 5

Nitrate metabolism capacity of strain NRRL 67118

| Function | Subsystem |
|---|---|
| Respiratory nitrate reductase gamma chain (EC 1.7.99.4) | Denitrifying reductase gene clusters; Nitrate and nitrite ammonification |
| Respiratory nitrate reductase delta chain (EC 1.7.99.4) | Denitrifying reductase gene clusters; Nitrate and nitrite ammonification |
| Respiratory nitrate reductase beta chain (EC 1.7.99.4) | Denitrifying reductase gene clusters; Nitrate and nitrite ammonification |
| Respiratory nitrate reductase alpha chain (EC 1.7.99.4) | Denitrifying reductase gene clusters; Nitrate and nitrite ammonification |
| Nitrate/nitrite transporter | Nitrate and nitrite ammonification |
| Nitrate/nitrite sensor protein (EC 2.7.3.—) | Nitrate and nitrite ammonification |
| Nitrite reductase [NAD(P)H] large subunit (EC 1.7.1.4) | Nitrate and nitrite ammonification |
| Nitrite reductase [NAD(P)H] small subunit (EC 1.7.1.4) | Nitrate and nitrite ammonification |
| Nitroreductase family protein | - none - |
| Putative nitroreductase family protein SACOL0874 | - none - |
| Oxygen-insensitive NAD(P)H nitroreductase (EC 1.—.—.—)/ Dihydropteridine reductase (EC 1.5.1.34) | - none - |
| Oxygen-insensitive NAD(P)H nitroreductase (EC 1.—.—.—)/ Dihydropteridine reductase (EC 1.5.1.34) | - none - |
| Nitroreductase family protein | - none - |
| Putative nitroreductase family protein SACOL0874 | - none - |
| Putative nitroreductase family protein SACOL0874 | - none - |
| Hydroxylamine reductase (EC 1.7.—.—) | Nitrosative stress |
| Oxygen-insensitive NADPH nitroreductase (EC 1.—.—.—) | - none - |

Strain NRRL 67118 is resistant to tetracyclin based on in vitro growth and analysis of the genome of this strain, which contains genes encoding ribosome protection-type tetracycline resistance related proteins (data not shown). The genome was also analyzed for the presence of virulence factors (e.g., toxins and superantigens). The analysis turned up nothing that would suggest that this strain is pathogenic to humans or animals. Analysis of the genome further revealed that the strain has pathways to produce bacitracin, which may explain its antimicrobial capacity.

The complete genome of *Paenibacillus* NRRL 67118 does not match anything in the database or literature, suggesting it represents a new species. Comparison with wild-type isolates indicates that this strain also contains a non-naturally-occurring (mutation-induced) capacity for $NO_3$ and $NO_2$ reduction.

Example 3

To determine whether strain NRRL 67118 could increase the capacity of ruminal microflora nitrate- and nitrite-reducing capacity, cultures with and without the addition of this strain were tested. Mixed population of ruminal microorganisms were inoculated into Medium B (described above, supplemented with differing concentrations of nitrate and nitrite either with or without the addition of strain NRRL 67118. Results are shown in FIG. 1.

The inoculation with strain NRRL 67118 to cultures containing 3 mM, 1.5 mM, and 0.5 mM $NO_2$ resulted in the $NO_2$ levels being decreased below the level of detection (5.0 nM) by 24 h incubation. By comparison, cultures containing 3 mM, 1.5 mM, and 0.5 mM $NO_2$ but without addition of strain NRRL 67118 showed only 19%, 77%, and 57%, respectively, reduction of $NO_2$ after 24 h incubation (FIG. 1, "probiotic" refers to addition of strain NRRL 67118).

Figure 2:
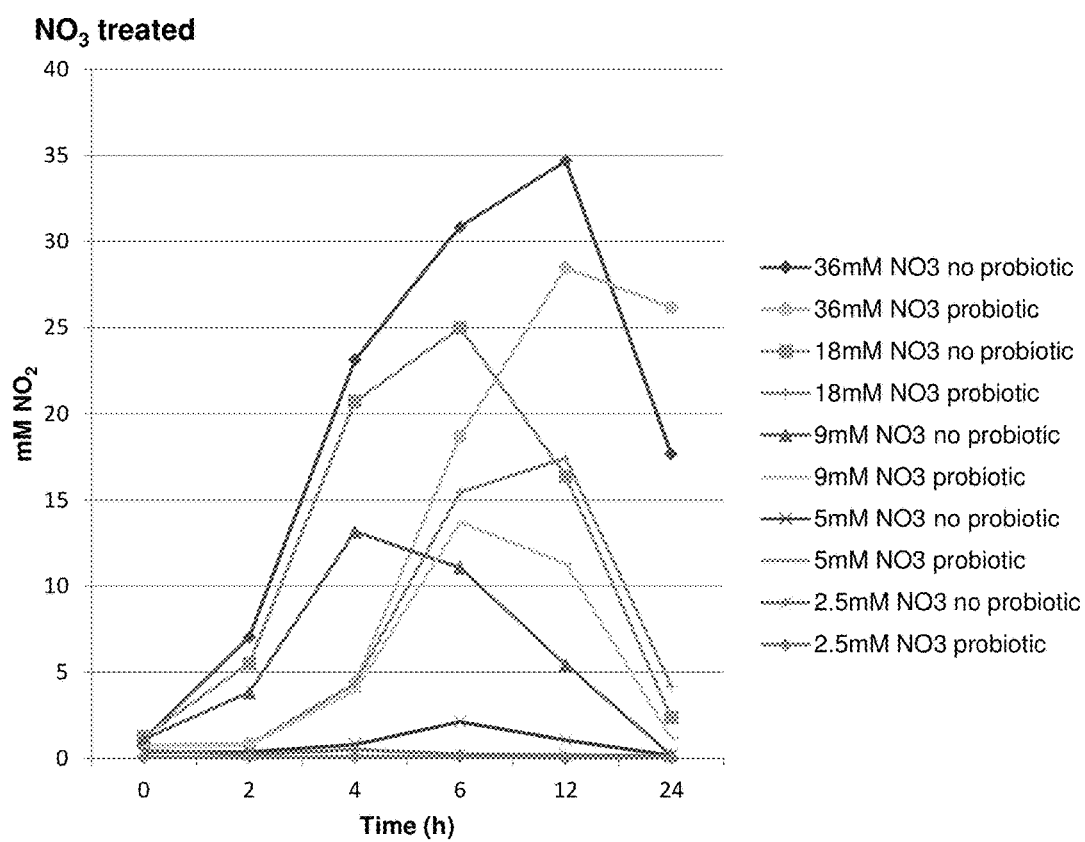
FIG. 2 provides a graph showing a reduction in peak nitrite accumulation in vitro in cultures supplemented or not with strain NRRL 67118.
Figure 3:
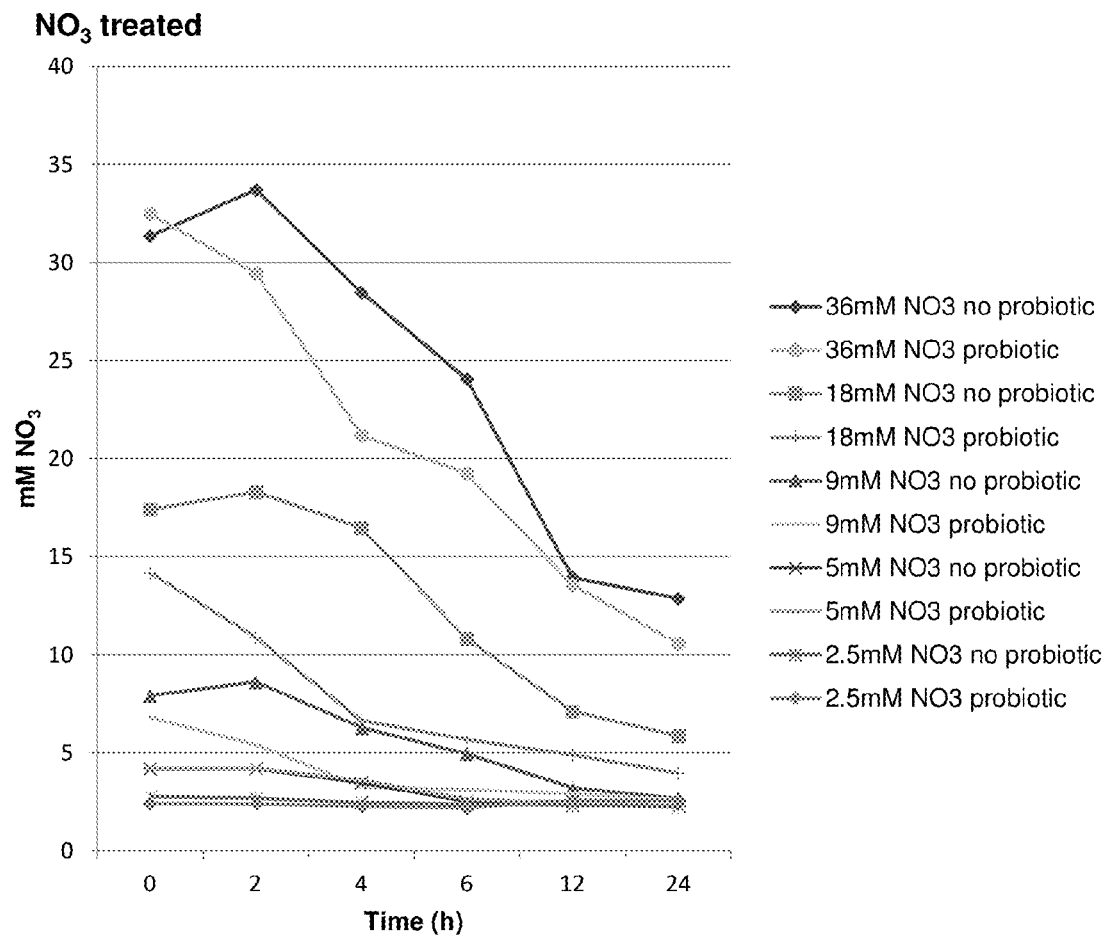
FIG. 3 provides a graph showing increased rapidity of reduction of nitrite in vitro in cultures supplemented or not with strain NRRL 67118.

The inoculation of strain NRRL 67118 into in vitro mixed ruminal cultures supplemented with 36 mM, 18 mM, 5 mM, and 2.5 mM $NO_3$ resulted in a reduction in peak $NO_2$ accumulation (FIG. 2) and a more rapid reduction compared to cultures with $NO_3$ alone (FIG. 3).

Example 4

Because it is known that high nitrate levels in ruminants can decrease methane production, strain NRRL 67118 was postulated as a potential probiotic feed additive that could protect against $NO_2$ intoxication in ruminants fed dietary $NO_3$ supplements to mitigate ruminal $CH_4$ production by consuming electrons for reduction of $NO_2$. Therefore, levels of methane in cultures containing nitrate and/or strain NRRL 67118 were examined.

Figure 4A:
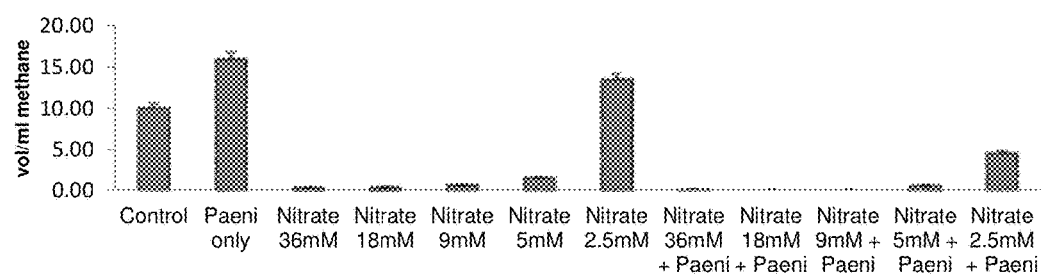
FIG. 4A provides a graph demonstrating the potential cumulative benefit of nitrate supplementation on methane production in vitro.
Figure 4B:
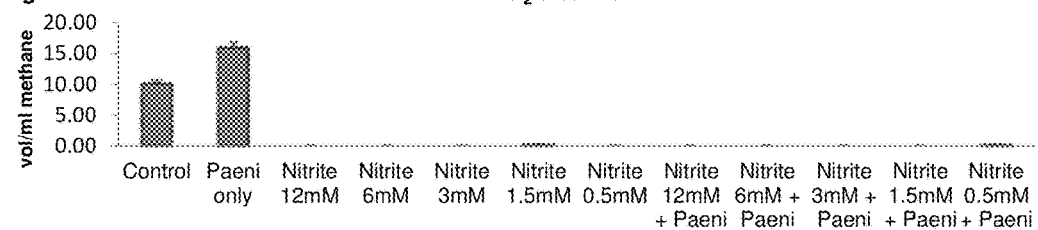
FIG. 4B provides a graph demonstrating the potential cumulative benefit of nitrite supplementation on methane production in vitro.

The results shown in FIGS. 4A and 4B demonstrate the potential cumulative benefit on $CH_4$ production in vitro of dietary $NO_3$ supplementation with strain NRRL 67118 probiotic incubated with mixed ruminal microorganisms. There was an interaction between the addition of $NO_3$ and strain NRRL 67118 strains on the total $CH_4$ production (p<0.05) (FIG. 4A). When strain NRRL 67118 was inoculated with 36 mM, 18 mM, 9 mM, 5 mM, and 2.5 mM of $NaNO_3$, a decrease in $CH_4$ production was observed compared with 36 mM, 18 mM, 9 mM, 5 mM, and 2.5 mM $NaNO_3$ alone (p<0.05).

No interaction between $NO_2$ and strain NRRL 67118 was observed. Regardless of strain NRRL 67118 addition, $CH_4$ production was found to be zero with the addition of 12 mM, 6 mM, 3 mM, 1.5 mM and 0.5 mM of $NaNO_2$ most likely because of the potent toxicity of $NO_2$ to methanogenic bacteria. Nevertheless, these results show that despite having high $NO_2$-reducing ability and thus high rates of $NO_2$ removal, cultures inoculated with strain NRRL 67118 still retained some residual $CH_4$-inhibiting activity as cultures inoculated with 1.5 mM $NO_2$ or 0.5 mM $NO_2$ with strain NRRL 67118 produced minimal amounts of $CH_4$ (FIG. 4B). Fermentation characteristics are shown in Table 6 for in vitro cultures supplemented with $NO_2$, $NO_3$, and/or strain NRRL 67118. No significant differences were observed across treatments thus indicating that strain NRRL 67118 synergistically enhances $CH_4$ mitigation and removal of $NO_2$ without redirecting electron flow to more reduced volatile fatty acid products.

TABLE 6

Effects of NRRL 67118, $NO_2$, $NO_3$, and their combination on fermentation in vitro.

| Product | No Additions | $NO_3$ | $NO_2$ | $NO_2$ + NRRL 67118 | $NO_3$ + NRRL 67118 |
|---|---|---|---|---|---|
| VFA | 195.00 | 192.00 | 198.00 | 201.00 | 207.00 |
| Formate | 0.59 | 17.29 | 13.86 | 13.47 | 18.72 |
| Acetate | 71.93 | 59.52 | 40.70 | 68.85 | 44.81 |
| Propionate | 33.06 | 17.46 | 8.56 | 16.11 | 9.37 |
| Butyrate | 11.26 | 7.24 | 4.90 | 7.05 | 5.33 |
| Other VFA | 45.77 | 68.18 | 70.46 | 68.33 | 73.42 |

Example 5

Five ruminally cannulated Holstein steers (786±29.3 kg) were separated by treatment into pens containing Bermuda grass. The animals had ad libitum access to water and forage. Experiment consisted of three controls days with no $NO_3$ or probiotic treatment, which was immediately followed by three days of $NO_3$ addition during which time 3 of the 5 steers were inoculated each morning and night with strain NRRL 67118. Rumen fluid, blood, and feces were collected 3 hours post feeding and treatment and at hours 0, 3, 6, and 12 post treatment on day 4. A 600 ml aqueous solution of 83 mg $NaNO_3$/kg body weight was given through fistulae split into two portions given twice daily (0700 and 1900 h). This dose is known to be a subclinical level of $NO_3$. The cells were inoculated to provide a concentration of $1 \times 10^6$ cells/ml of rumen content given through fistulae in two portions likewise given twice daily at 0700 and 1900 h. Blood was collected via the jugular to determine methemoglobin levels. Rumen and fecal samples were inoculated in vitro to determine ruminal $CH_4$-producing activity and $NO_3$- and $NO_2$-reducing activity. Rumen fluid and in vitro cultures were analyzed via colorimetric assays and gas chromatography.

Results presented (Table 5) demonstrate that $NO_3$ and $NO_2$ were not detected in the rumen of steers dosed twice daily with a daily dose of 83 mg $NaNO_3$/kg body weight at any sampling time. A likely reason $NO_3$ and $NO_2$ did not accumulate in these steers is that they had been grazing a pasture where the forage already had $NO_3$ accumulation (0.39% forage dry matter) and thus likely already had been naturally selected to have endogenous microbial populations with higher than normal $NO_3$ reducing activity. Nevertheless, blood methemoglobin levels in animals treated with both strain NRRL 67118 and nitrate was significantly lower on days 4 and 5 (2 and 3 days following the first treatment) compared to animals treated with nitrate alone (data not shown). Methemoglobin levels were determined using previously described methodology (Cruz-Landeira et al., J. Analyt. Toxicol., (2002) 26:67-72). Moreover, activities of $NO_3$ and $NO_2$ reduction were significantly greater in steers treated with strain NRRL 67118 as compared to controls and $NO_3$ only treated steers (Table 7, subscripts denote statistically significant differences). Control measurements were measured in the same five steers the day immediately prior to initiation of the treatments. This indicates that inoculation with strain NRRL 67118 provided protection above and beyond that which could be obtained via natural adaptation of the steers to diets containing upwards of 181 mg $NO_3$/kg DM.

The experiment was approved by the Southern Plains USDA Animal Use and Care protocol.

TABLE 7

Effect of $NO_3$ addition on $CH_4$-producing activity
and $NO_2$- and $NO_3$-reducing activity.

| Treatment | $dCH_4/dt$ (umol/ml per h) | Nitrite reduction (mM/hr) | Nitrate reduction (mM/hr) |
|---|---|---|---|
| Control | 4.13 a | 1.21 c | 0.42 e |
| Nitrate only | 2.22 b | 1.38 c | 0.54 e |
| NRRL 67118 + Nitrate | 2.15 b | 1.66 d | 0.76 f |

The experiment was approved by the Southern Plains USDA Animal Use and Care protocol.

Example 6

Denitrification is the dissimilatory reduction of nitrate or nitrite to the gaseous end product nitrogen gas with nitrous and nitric oxide as intermediates. Evaluation of the whole genome sequence of strain NRRL 67118 revealed the presence of all the genes necessary to support a complete functional denitrification pathway whereby nitrate would be completely reduced to nitrogen gas for energy production. This is in contrast to *Propionibacterium acidipropionici* which is known to reduce nitrate to ammonia and nitrite to nitrous oxide, supposedly as a mechanism to detoxify nitrite rather as an energy conservation mechanism (Kaspar, Arch. Microbiol., (1982) 133:126-30).

To determine the fate of nitrogen, strain NRRL 67118 was inoculated at $10^6$ cells/ml into 18×150 mm crimp top tubes containing medium B (prepared under 100% $CO_2$ plus 32 mM sodium formate as reductant) treated with either nitrate (10 mM) or nitrite (5 mM). Cultures (n=4 per treatment) were incubated at 39° C. for 24 h without agitation.

Culture fluid samples were collected at 0 and 24 h for colorimetric determination of nitrite, ammonia, and nitrate concentration. After 24 h incubation, gas ($CH_4$, $CO_2$, $H_2$, and $CH_4$) production was measured by volume displacement and measured via gas chromatography (Allison et al., Syst. Appl. Microbiol., (1992) 15:522-29). Amounts produced were calculated as the difference between final and initial concentrations and are shown in Table 8 (μmol/mL).

Strain NRRL 67118 is capable of anaerobic growth by carrying out denitrifying metabolism using nitrate or nitrite as terminal electron acceptors. Analysis of the genome revealed that this strain does possess all reductases necessary to reduce $NO_3$ completely to $N_2$. As such, nitrogen gas is the predominant end-product produced by the bacteria when it is incubated with added nitrite in medium B containing 5 mM $NO_2$ and 100 $CO_2$, with approximately 78% of the N in the 4.26 μmol $NO_2$/mL gas metabolized being recovered in $N_2$ gas (1.66 μmol $N_2$/mL which equates to the consumption of 3.32 μmol N atoms). Change in concentration (μmol/mL) after 24 h incubation (mM) is shown in Table 8. When strain NRRL 67118 is incubated with added nitrate, nearly all the nitrate is metabolized to nitrite which is also nearly all catabolized to an as of yet unknown product(s) thus suggesting that the presence of nitrate may be a strong suppressor of nitrite reductase expression (Table 8).

TABLE 8

Effects of NRRL 67118 ("Pb"), $NO_2$, $NO_3$, and its
combination on gas production in in vitro cultures

| | No additions | Std Dev | Pb & $NO_3$ | Std Dev | Pb & $NO_2$ | Std Dev | Pb & formate | Std Dev |
|---|---|---|---|---|---|---|---|---|
| Total gas (mL) | −3.00 | 0 | +4.50 | 0 | +4.50 | 0 | +3.50 | 0.71 |
| $H_2$ produced | +0.51 | 0.06 | +0.40 | 0.12 | +0.60 | 0.01 | +0.73 | 0.07 |
| $N_2$ produced | +0.00 | 0 | +0.23 | 0.01 | +1.66 | 0.03 | +0.61 | 0.12 |
| $NO_2$ metabolized | −0.50 | 0.01 | +0.01 | 0.01 | −4.26 | 0.13 | 0.00 | 0 |
| $NO_3$ metabolized | −0.11 | 0.23 | −3.13 | 1.08 | −0.71 | 0.24 | −0.37 | 0.13 |
| $NH_3$ formed | −0.03 | 0.01 | +2.37 | 0.03 | +2.22 | 0.01 | +2.07 | 0.02 |

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A composition comprising the biologically pure *Paenibacillus* bacterial strain NRRL 67118.

2. The composition of claim 1, further comprising a carrier feed composition suitable for ingestion by a ruminant.

3. The composition of claim 2, wherein the carrier feed composition is hay, silage, or forage.

4. The composition of claim 2, wherein the ruminant is selected from the group consisting of cattle, sheep, and goats.

5. The composition of claim 2, further comprising a nitrate salt.

6. The composition of claim 5, wherein the nitrate salt is sodium nitrate, potassium nitrate, calcium nitrate, or ammonium nitrate.

7. The composition of claim 2, wherein the carrier feed composition is a compound feed.

8. The composition of claim 2, wherein bacterial strain NRRL 67118 is present in an amount from $10^2$ to $10^{20}$ colony forming units per kilogram of dry weight carrier feed.

9. The composition of claim 1, further comprising a premix or a lick block.

10. The composition of claim 9, further comprising a nitrate salt.

11. The composition of claim 10, wherein the nitrate salt is sodium nitrate, potassium nitrate, calcium nitrate, or ammonium nitrate.

12. The composition of claim 9, wherein bacterial strain NRRL 67118 is present in an amount from $10^2$ to $10^{20}$ colony forming units per kilogram of the premix or lick block.

13. A method of reducing nitrate/nitrite toxicity in a ruminant, comprising introducing or maintaining in the ruminant's rumen a population of the biologically pure *Paenibacillus* bacterial strain NRRL 67118 which is capable of anaerobic denitrification of the rumen.

14. The method of claim 13, wherein the population is introduced or maintained by feeding the ruminant a carrier feed composition, a premix, or a lick block containing the biologically pure bacterial strain NRRL 67118.

15. The method of claim 14, wherein bacterial strain NRRL 67118 is present in an amount from $10^2$ to $10^{20}$ colony forming units per kilogram of dry weight of the carrier feed composition, premix, or lick block.

16. The method of claim 13, wherein the population is introduced or maintained by feeding the ruminant the bacterial strain NRRL 67118 such that the microbe is delivered in an amount of from $10^2$ to $10^{20}$ colony forming units per milliliter of ruminal fluid per day.

17. The method of claim 16, wherein the feeding occurs for a period of 1 to 10 days.

18. The method of claim 13, wherein the population is introduced or maintained by providing the ruminant a water source containing the biologically pure bacterial strain NRRL 67118.

19. The method of claim 18, wherein the strain is present in the water source at a concentration of from $10^2$ to $10^{20}$ colony forming units per liter.

20. A method of preventing nitrate/nitrite toxicity in a ruminant susceptible to such toxicity, comprising introducing or maintaining in the ruminant's rumen a population of the biologically pure *Paenibacillus* bacterial strain NRRL 67118 which is capable of anaerobic denitrification of the rumen.

21. The method of claim 20, wherein the population is introduced or maintained by feeding the ruminant a carrier feed composition, a premix, or a lick block containing the biologically pure bacterial strain NRRL 67118.

22. The method of claim 21, wherein bacterial strain NRRL 67118 is present in an amount from $10^2$ to $10^{20}$ colony forming units per kilogram of dry weight of the carrier feed composition, premix, or lick block.

23. The method of claim 20, wherein the population is introduced or maintained by feeding the ruminant the bacterial strain NRRL 67118 such that the microbe is delivered in an amount of from $10^2$ to $10^{20}$ colony forming units per milliliter of ruminal fluid per day.

24. The method of claim 23, wherein the feeding occurs for a period of 1 to 10 days.

25. The method of claim 20, wherein the population is introduced or maintained by providing the ruminant a water source containing the biologically pure bacterial strain NRRL 67118.

26. The method of claim 25, wherein the strain is present in the water source at a concentration of from $10^2$ to $10^{20}$ colony forming units per liter.

27. A method of reducing gastrointestinal methanogenesis in a ruminant, the method comprising administering to the ruminant a composition comprising an effective amount of a nitrate compound and introducing or maintaining in the ruminant's rumen a population of the biologically pure *Paenibacillus* bacterial strain NRRL 67118 which is capable of anaerobic denitrification of the rumen.

28. The method of claim 27, wherein the nitrate compound is sodium nitrate, potassium nitrate, calcium nitrate, or ammonium nitrate.

29. The method of claim 27, wherein the nitrate compound is present in the composition in an amount of 1 to 100 grams per kilogram of dry weight.

30. The method of claim 27, wherein the population is introduced or maintained by feeding the ruminant a carrier feed composition, a premix, or a lick block containing the biologically pure bacterial strain NRRL 67118.

31. The method of claim 30, wherein bacterial strain NRRL 67118 is present in an amount from $10^2$ to $10^{20}$ colony forming units per kilogram of dry weight of the carrier feed composition, premix, or lick block.

32. The method of claim 27, wherein the population is introduced or maintained by feeding the ruminant the bacterial strain NRRL 67118 such that the microbe is delivered in an amount of from $10^2$ to $10^{20}$ colony forming units per milliliter of ruminal fluid per day.

33. The method of claim 27, wherein the population is introduced or maintained by providing the ruminant a water source containing the biologically pure bacterial strain NRRL 67118.

34. The method of claim 33, wherein the strain is present in the water source at a concentration of from $10^2$ to $10^{20}$ colony forming units per liter.

35. The method of claim 27, wherein the administering step and the introducing or maintaining step occur concomitantly.

36. A method of reducing a food-borne pathogen in a ruminant, comprising introducing or maintaining in the ruminant's rumen a population of the biologically pure *Paenibacillus* bacterial strain NRRL 67118 which is sufficient to reduce the pathogen, wherein the pathogen is *E. coli* or *C. jeiuni*.

37. The method of claim 36, wherein the population is introduced or maintained by feeding the ruminant a carrier feed composition, a premix, or a lick block containing the biologically pure bacterial strain NRRL 67118.

38. The method of claim 37, wherein bacterial strain NRRL 67118 is present in an amount from $10^2$ to $10^{20}$ colony forming units per kilogram of dry weight of the carrier feed composition, premix, or lick block.

* * * * *